United States Patent [19]

Schlingmann et al.

[11] Patent Number: 4,709,086

[45] Date of Patent: Nov. 24, 1987

[54] PROCESS FOR THE PREPARATION OF 4-BENZYL ASPARTATE

[75] Inventors: Merten Schlingmann, Königstein; Hans-Ullrich Hoppe, Hofheim am Taunus; Walter Dürsch, Königstein, all of Fed. Rep. of Germany

[73] Assignee: Hoechst Aktiengesellschaft, Frankfurt am Main, Fed. Rep. of Germany

[21] Appl. No.: 872,250

[22] Filed: Jun. 9, 1986

[30] Foreign Application Priority Data

Jun. 11, 1985 [DE] Fed. Rep. of Germany ....... 3520808

[51] Int. Cl.$^4$ ........................................... C07C 101/22
[52] U.S. Cl. ..................................................... 560/171
[58] Field of Search ......................................... 560/171

[56] References Cited

U.S. PATENT DOCUMENTS 4,394,308 7/1983 Sampathkumar et al. ........ 260/112.5

FOREIGN PATENT DOCUMENTS 2608174 7/1977 Fed. Rep. of Germany .
37-13976 9/1962 Japan .................................. 560/171

OTHER PUBLICATIONS

Levenspiel, "Chemical Reaction Engineering," 2nd Ed., pp. 185-199, (1972).
McOmie, "Protective Groups in Organic Chemistry," pp. 196-198 & 210-215, (1973).
Smith, J. Pharm. Sci., 54, pp. 1269-1273, (1965).
Heeswijk, Synthesis, pp. 744-747, (1982).
Howben-Weyl, 15/1, p. 349, (1974).
Prestidge, J. Org. Chem., 40, pp. 3287-3288, (1975).

Primary Examiner—Michael L. Shippen
Attorney, Agent, or Firm—Curtis, Morris & Safford

[57] ABSTRACT

In the process for the preparation of 4-benzyl aspartate starting from dibenzyl aspartate and/or its salts only one benzyl group is selectively removed by catalytic hydrogenation. By setting up appropriate reaction conditions elimination takes place mainly of the benzyl group on the $C_1$ atom of the compound. The desired product can be isolated from the reaction mixture by precipitation.

8 Claims, No Drawings

PROCESS FOR THE PREPARATION OF 4-BENZYL ASPARTATE

4-Benzyl L-aspartate is of interest as an intermediate for a synthesis of the sweetener L- -aspartyl-L-phenyl alanine methyl ester ("Aspartame"). 4-Benzyl aspartate has hitherto, as described in U.S. Pat. No. 4,394,308, been prepared directly from aspartic acid, benzyl alcohol and sulfuric acid by a process in which large amounts of ethanol, diethyl ether and an organic base such as pyridine or triethylamine are used. Because of the large and unavoidable losses of solvents and adverse effects on the environment, this route can be followed on the industrial scale only with extremely elaborate apparatus. Various other processes starting from dibenzyl L-aspartate also exhibit considerable disadvantages such as, for example, the necessity to use copper salts or lithium hydroxide (J. Org. Chem. 40, 3287, 1975; Synthesis, 744, 1982; German Offenlegungsschrift 2,608,174), which make industrial use very difficult or costly.

Thus, there was interest in a straightforward process for the preparation of 4-benzyl aspartate, which is both environmentally acceptable and can be carried out industrially without problems.

It is known that the elimination of benzyl ester radicals by hydrogenolysis results in free carboxyl groups with the formation of toluene. However, it could not have been expected that hydrogenation of dibenzyl aspartate and its salts can be directed predominantly towards 4-benzyl aspartate, especially since 1-benzyl aspartate is also obtained from the tosylate of benzyl aspartate under specific conditions (Houben-Weyl, 15/1, page 349).

Surprisingly, a straightforward process for the preparation of 4-benzyl aspartate has now been found, in which, starting from dibenzyl aspartate or its salts, only one benzyl group, mainly the 1-benzyl radical, is selectively removed by hydrogenation under the chosen conditions. A mixture of products results, from which the desired product can be removed by precipitation.

Thus, the invention relates to a process for the preparation of the compound of the formula I

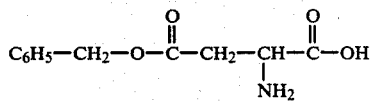

and its salts, which comprises catalytic hydrogenation of a compound of the general formula II

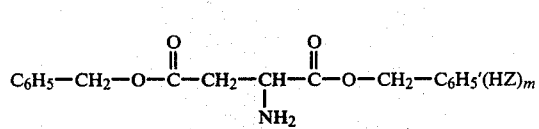

in which
Z is an inorganic or organic acid equivalent, and
m is 0 or 1, in an aqueous and/or organic medium.

Preferred embodiments of the invention are detailed in the description which follows and in the Patent claims.

Dibenzyl aspartate can be prepared straightforwardly and in good yields in the form of a tosylate, in analogy to Houben-Weyl 15/1, page 348, by azeotropic removal of water from aspartic acid and benzyl alcohol using benzenesulfonic or p-toluenesulfonic acid as catalyst and toluene as the water-entraining agent. It is possible to liberate the basic diester from the tosylate of dibenzyl aspartate which has been produced in this manner by use of alkaline compounds and to convert it into other salts.

The various salts of dibenzyl aspartate or the free base can be used as starting materials either as homogeneous substances or as mixtures. Preference is given to the tosylate of dibenzyl aspartate, because it is directly accessible without problems, and to the salts with benzenesulfonic acid.

Depending on the nature of the starting material used, suitable diluents are water and/or solvents which are miscible with water, such as lower alcohols, tetrahydrofuran, dioxane, acetone and acetonitrile, but also solvents which are insoluble in water, such as the esters methyl, ethyl or n-butyl acetate or the hydrocarbons or chlorinated hydrocarbons such as toluene, chlorobenzene or methylene chloride. Preference is given to water or monohydric alcohols having 1 to 3 carbon atoms, where appropriate, mixed with water, as well as toluene because it is also produced in the reaction.

The choice of the diluent is determined by the solubility of the starting material used, and which should be high as possible. The inorganic salts of dibenzyl aspartate, as well as, for example, its acetate and its formate, are readily soluble in water and lower alcohols, whereas they can be dissolved only with difficulty in hydrophobic solvents. The salts with benzenesulfonic acid and p-toluenesulfonic acid dissolve both in hot water and in lower alcohols at elevated temperature and mixtures of lower alcohols with water at elevated temperature. The free basic diester is taken up by most organic solvents but not by water.

The starting compound should from the outset be dissolved as completely as possible. If this is impossible, subsequent addition of portions in the form of a solution can be done. During the reaction, the reaction mixture should be homogeneous, at least transiently, in order to achieve better conversion of the diester and a good yield of 4-benzyl aspartate, at the same time the production of undesired aspartic acid and 1-benzyl aspartate being suppressed.

Hydrogenation is carried out with hydrogen in amounts of from 0.7 to 1.3 mol, preferably 0.9 to 1.1 mol. Suitable hydrogenation catalysts are, for example, the metal catalysts listed in Organikum (1970), page 314, suoh as palladium, palladium chloride, platinum and Raney nickel. Palladium/charcoal with palladium contents of from 5 to 10% is preferred. 0.1–2.0%, preferably 0.2–1.0%, of palladium/charcoal (containing 5% palladium), based on the starting material, are required. The hydrogenation can be carried out without problems in every conventional hydrogenation apparatus on the laboratory, pilot-plant and production scale.

The gage pressures of hydrogen may vary between about 0.01 and 50 bar, preferably between 0.02 and 2 bar. The reaction temperatures can range from −30° C. to 150° C., preferably 0° C. to 80° C. In most cases a temperature of 20°–60° C. is especially suitable. The reaction times are between 10 minutes and 48 hours, preferably between 30 minutes and 16 hours. In the presence of water there may be partial hydrolytic elimination of benzyl alcohol at elevated temperatures.

Depending on the particular process, the reaction products which result are contaminated by variable amounts of 1-ester, diester, benzyl alcohol and toluene, and these must be removed. The method of purification depends on the nature of the starting material and of the diluent. If a salt of dibenzyl aspartate has been used as the starting material then, owing to the liberation of one carboxyl group per molecule, strongly acidic salts of 4-benzyl aspartate result. These are readily soluble in water and/or solvents which are miscible with water. The desired 4-benzyl aspartate can, after the hydrogenation catalyst has been removed by filtration with suction, be selectively precipitated, as the least soluble internal salt, from solutions of this type by addition of neutralizing agents, for example by alkaline metal or alkaline earth metal hydroxides, methylates, carbonates or bicarbonates, preferably sodium hydroxide solution, at pH values of about 2-7. If, after the precipitates have been filtered off with suction and dried, the desired degree of purity has not yet been reached, then any contaminating 1-benzyl or dibenzyl ester which is still present can be removed by recrystallization from 12-20 times the amount of water.

Small amounts of impurities can also be eliminated from the more sparingly soluble 4-ester by cold or hot extraction using about 2-5 times the amount of water. Prolonged periods at pH values below 2 and, especially, above 6 or 7 should be avoided, particularly at elevated temperatures, since they may result in hydrolytic elimination of the benzyl ester.

If the free basic diester is used as starting material, then the hydrogenation directly results in 4-benzyl aspartate, where appropriate, together with some 1-benzyl and dibenzyl aspartate, as an internal salt which is sparingly soluble in most solvents. This salt can be, for example, removed together with the hydrogenation catalyst, which is likewise insoluble, by filtration with suction. The filtrate contains only small amounts of benzyl alcohol together with the diluent and the toluene produced in the reaction. The gray filter cake can either be recrystallized from water or dissolved as the hydrochloride of 4-benzyl aspartate, for example by use of molar amounts of hydrochloric acid, and, after removal of the insoluble hydrogenation catalyst by filtration with suction, be precipitated again by adjustment to a pH of 2-7, preferably 3-6, and removed by filtration with suction. The purified 4-benzyl aspartate which is still moist can be dried in a customary manner, for example in a desiccator or in a vacuum drying oven, under a vacuum of 50-400 mbar and at temperatures of 40°-100° C., preferably 50°-90° C.

The purity of the resulting 4-benzyl aspartate can be checked by $^1$H NMR spectroscopy and/or HPLC analyses.

The process according to the invention is environmentally acceptable and can be carried out industrially without problems. A 4-benzyl L-aspartate which has been prepared in this manner and has adequate purity can be used, for example, directly for the preparation of Aspartame.

The intention is to illustrate, but not to restrict, the invention by the examples which follow. In many of the examples the starting compound is used in the L-form. Of course, it is also possible to use the D- or D,L-form. The stereoisomeric forms and the racemate are interchangeable at will.

EXAMPLES

The HPLC analysis in all examples is carried out on reverse phase silica gel which has been silylated with alkyl radicals having 8 carbon atoms (RP8), and using a methanol/water (1:1, v:v) mobile phase at a pH of 2.8.

EXAMPLE 1

In a laboratory hydrogenation apparatus, a mixture of 97.1 g (0.2 mol) of the tosylate of dibenzyl L-aspartate, 200 g of methanol, 100 g of water and 0.8 g of palladium/charcoal (5% palladium) is heated at 45° C. under nitrogen. The salt dissolves during this, the apparatus is evacuated, the vacuum is abolished with hydrogen, and the same procedure is repeated. 4,600 ml of hydrogen are passed in at 40° C. over the course of 100 minutes. After the hydrogenation catalyst has been removed by filtration with suction, a pH of 5.5 is set up by addition of 25.5 g of 33% strength sodium hydroxide solution using a glass electrode. A colorless precipitate results, and this is removed by filtration with suction and washed twice with 50 ml of water each time. After drying in a vacuum drying oven at 70° C., 31.6 g of crude 4-benzyl L-aspartate are obtained, and this is further purified by trituration with 200 ml of water. After the insoluble residue has been removed by filtration with suction and drying in a vacuum drying oven at 70° C., the result is 26.4 g (59.1% of theory) of 4-benzyl L-aspartate which is pure as shown by H-NMR and HPLC.

EXAMPLE 2

The process is carried out as in Example 1 but the diluent used is a mixture of 300 g of isopropanol and 120. g of water. At 45° C., the 4,600 ml of hydrogen are taken up in 50 minutes. The result is 29.8 g of crude product and 24.4 g (54.7% of theory) of pure 4-benzyl L-aspartate.

EXAMPLE 3

The process is carried out in analogy to Example 1 but the diluent used is a mixture of 200 g of tetrahydrofuran and 200 g of water. Hydrogenation is carried out at 28° C. for 120 minutes. A pH of 6 is set up with 28.4 g of 33% strength sodium hydroxide solution. After drying, 21.2 g of crude product and 19.2 g (43.0% of theory) of pure 4-benzyl L-aspartate are obtained.

EXAMPLE 4

The process is carried out as in Example 1 but the diluent used is 300 g of methanol. Hydrogenation with 4,600 ml of hydrogen is carried out at 40° C. in 40 minutes. After the hydrogenation catalyst has been removed by filtration with suction, 36.0 g of a 30% strength solution of sodium methylate in methanol are added dropwise at room temperature. The resulting colorless precipitate is removed by filtration with suction and washed twice with 60 g of methanol each time. After drying, 29.1 g (65.7% of theory) of pure 4-benzyl L-aspartate are obtained.

EXAMPLE 5

In a laboratory hydrogenation apparatus a mixture of 48.6 g (0.1 mol) of the tosylate of dibenzyl L-aspartate, 150 g of acetone, b 100 g of water and 0.4 g of palladium/charcoal (5% palladium) is heated under nitrogen at 30° C. After the tosylate has dissolved the apparatus is evacuated, the vacuum is abolished with hydrogen, and this procedure is repeated. After uptake of 2,300 ml of hydrogen, which is complete after 120 minutes, the hydrogenation catalyst is removed by filtration with suction, and the pH of the filtrate is adjusted to 5.6 with 14.0 g of 33% strength sodium hydroxide solution. After filtration with suction and drying in a vacuum drying oven at 70° C., 9.1 g (40.7% of theory) of 4-benzyl L-aspartate are obtained.

EXAMPLE 6

The process is carried out as in Example 5 but the diluent used is a mixture of 100 g of dioxane and 100 g of water. Hydrogenation is carried out with 2,300 ml of hydrogen at 45° C. in 150 minutes. After the hydrogenation catalyst has been removed by filtration with suction, 14.7 g of 33% strength sodium hydroxide solution are added. This results in a pH of 5.6 and a precipitate which is triturated with 50 ml of water, removed by filtration with suction and dried in a vacuum drying oven at 70° C. 10.7 g (47.9% of theory) of pure 4-benzyl L-aspartate are obtained.

EXAMPLE 7

The process is carried out as in Example 5 but the diluent used is 300 g of water at 60° C. The tosylate is only partially dissolved at the start of the hydrogenation but dissolves during the course of the uptake of 2,300 ml of hydrogen, which takes place in a total of 6 hours. The reaction product comprises three phases. The middle aqueous phase is isolated and adjusted to a pH of 5.5 with 12.0 g of 33% strength sodium hydroxide solution. The colorless precipitate is removed by filtration with suction, triturated with 60 ml of water, again removed by filtration with suction and dried in a vacuum drying oven at 70° C. 11.0 g (49.3% of theory) of pure 4-benzyl L-aspartate are obtained.

EXAMPLE 8

The process is carried out as in Example 5 but the diluent used is 150 g of acetonitrile and 50 g of water. Hydrogenation is carried out with 2,300 ml of hydrogen at 30° C. in 80 minutes. After the catalyst has been removed by filtration with suction, the pH is set at 5.5 using 14.6 g of 33% strength sodium hydroxide solution. The precipitate is triturated with 50 ml of water, again removed by filtration with suction and dried. The result is 5.8 g (26% of theory) of pure 4-benzyl L-aspartate.

Because of the relatively high solubility of 4-benzyl L-aspartate in the solvent mixture, the filtrate is concentrated to 72 g under waterpump vacuum. After addition of 50 ml of water, the precipitate is removed by filtration with suction, triturated with 50 ml of water and again removed by filtration with suction. The same procedure is repeated. The residue which then results on the filter is dried. A further 3.6 g (16.1% of theory) of pure 4-benzyl L-aspartate are obtained.

EXAMPLE 9

The process is carried out as in Example 5 but the diluent used is a mixture of 100 g of toluene and 100 g of water. Hydrogenation is carried out with 2,300 ml of hydrogen at 50° C. in 90 minutes. After the catalyst has been removed by filtration with suction the toluene phase is separated off. The lower aqueous phase is adjusted to a pH of 5.7 using 14.8 g of 33% strength sodium hydroxide solution. The precipitate which has separated out is triturated with 50 ml of water and removed by filtration with suction and dried in a vacuum drying oven at 70° C. 12.6 g (56.5% of theory) of pure 4-benzyl L-aspartate are obtained.

EXAMPLE 10

97.1 g (0.2 mol) of the tosylate of dibenzyl L-aspartate, 250 g of toluene, 200 g of water and 89.7 g (0.25 mol) of 4M sodium hydroxide solution are vigorously mixed in a separating funnel. After separation of the phases, the lower aqueous phase is extracted once more with 100 g of toluene, and the toluene extract is added to the first toluene upper phase. 0.4 g of palladium/charcoal (5% Pd) is added to the combined toluene phases which contain the basic diester. The mixture is then heated to 50° C., and the contents of the flask are, after displacement of the nitrogen by hydrogen described in Example 1, hydrogenated with 4,500 ml of hydrogen within 21 hours. A further 0.2 g of hydrogenation catalyst is added after 8 and after 16 hours. The precipitated crude 4-benzyl L-aspartate is removed together with the catalyst by filtration with suction. Toluene is completely removed from the filter cake, which is taken up in 600 ml of hot water. After the insoluble catalyst has been removed, pure 4-benzyl L-aspartate crystallizes out. It is filtered off with suction and dried in a vacuum drying oven at 70° C. 22.5 g (50.4% of theory) of pure 4-benzyl L-aspartate are obtained.

EXAMPLE 11

The process is carried out as in Example 10 but 100 g of water are added to the toluene phase before hydrogenation. Hydrogenation is carried out with 4,500 ml of hydrogen at 25° C. in 120 minutes. The crude 4-benzyl L-aspartate is removed together with the catalyst by filtration with suction, and the product is recrystallized from 600 ml of water at 90° C. The result after filtration with suction and drying is 20.4 g (45.7% of theory) of pure 4-benzyl L-aspartate.

EXAMPLE 12

The process is carried out as in Example 10 but 80 ml of water and 13.3 g (0.05 mol) of 4M hydrochloric acid are added to the toluene phase before the hydrogenation. The hydrogenation is carried out at 30° C. and is complete after 110 minutes. The precipitated crude product is recrystallized from 600 ml of water. 21.0 g (47.0% of theory) of pure 4-benzyl L-aspartate are obtained.

EXAMPLE 13

The process is carried out as in Example 10 but 53.1 g (0.2 mol) of hydrochloric acid are added to the toluene phase before the hydrogenation. The hydrogenation is carried out at 28° C. and is complete after 100 minutes. After addition of 100 ml of water, the catalyst is removed by filtration with suction, and the filtrate is adjusted to a pH of 4.0 using 63.1 g of 4M sodium hydroxide solution. The precipitate which has separated out is removed by filtration with suction and dried in a vacuum drying oven at 70° C. The result is 22.3 g (49.9% of theory) of pure 4-benzyl L-aspartate.

EXAMPLE 14

3.5 g (10 mmol) of the hydrochloride of dibenzyl L-aspartate, 20 g of water, 20 ml (20 mmol) of 1M hydrochloric acid and 0.1 g of palladium/charcoal (5% palladium content) are hydrogenated with 230 ml of hydrogen at 25° C. in 160 minutes. After the hydrogenation catalyst has been removed by filtration with suction, 7.6 g of 4M sodium hydroxide solution are added. This results in a precipitate separating out, and this is removed by filtration with suction and dried. 1.04 g (46.6% of theory) of pure 4-benzyl L-aspartate are obtained.

EXAMPLE 15

17.5 g (50 mmol) of the hydrochloride of dibenzyl D,L-aspartate, 130 g of water, 2.5 ml (10 mmol) of 4M hydrochloric acid and 0.2 g of palladium/charcoal (5% Pd) are hydrogenated with 1,160 ml of hydrogen at 35° C. in 170 minutes. After the hydrogenation catalyst has been removed by filtration with suction the filtrate is adjusted to a pH of 5.8 using 17.2 g of 4M sodium hydroxide solution. The precipitate is removed by filtration with suction and dried. 6.5 g (58.2% of theory) of pure 4-benzyl D,L-aspartate are obtained.

EXAMPLE 16

The process is carried out as in Example 5 but the tosylate of dibenzyl D,L-aspartate is used, and 100 g of methanol and 100 g of water are used as the diluent. Hydrogenation with 2,300 ml of hydrogen is carried out at 40° C. in 110 minutes. The hydrogenation catalyst is removed by filtration with suction, and the filtrate is adjusted to a pH of 5.6 using 13.2 g of 33% strength sodium hydroxide solution. The colorless precipitate is removed by filtration with suction. After drying in a vacuum drying oven at 70° C. 11.0 g (49.3% of theory) of pure 4-benzyl D,L-aspartate are obtained.

We claim:

1. A process for the preparation of a compound of the formula I

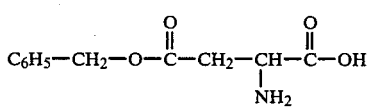

and of its salts, which comprises catalytic hydrogenation of a compound of the formula II

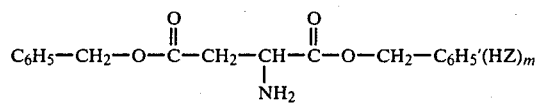

in which

Z is an inorganic or organic acid equivalent, and
m is 0 or 1, in a liquid aqueous or a liquid organic medium or a combination thereof using 0.7 to 1.3 mol of hydrogen per mole of compound of formula II under a gage pressure of 0.01 to 50 bar at a reaction temperature of −30° to 150° C., and which further comprises isolation of the compound of formula I by precipitation at pH values of from 2 to 7.

2. The process as claimed in claim 1, wherein use is made of a compound of the formula II in which Z is chloride or the radical of benzenesulfonic or p-toluenesulfonic acid.

3. The process as claimed in claim 1, wherein the liquid medium used is water or an alcohol having 1 to 3 carbon atoms or a combination thereof.

4. The process as claimed in claim 1, wherein hydrogenation is carried out with 0.9 to 1.1 mol of hydrogen under a gage pressure of 0.02 to 2 bar and at a reaction temperature of 0° to 80° C.

5. The process as claimed in claim 4, wherein hydrogenation is carried out at a reaction temperature of 20° to 60° C.

6. The process as claimed in claim 1, wherein the compound of the formula I is isolated by precipitation at pH values of from 3 to 6.

7. The process as claimed in claim 1, wherein m is 1 and the catalytic hydrogenation is carried out in a liquid aqueous medium and the catalyst is removed by filtration after the hydrogenation and before isolating the compound of formula I from the filtrate.

8. The process as claimed in claim 1, wherein m is 0 which further comprises carrying out the catalytic hydrogenation in a liquid organic medium, filtering the reaction mixture after the hydrogenation to obtain a filter cake and obtaining the compound of formula I by either recrystallizing the filter cake from water or by dissolving the filter cake in an acidic aqueous medium, followed by removing the insoluble hydrogenation catalyst by filtration and precipitating the compound of formula I by adjusting the pH of the filtrate to a value of from 2 to 7.

* * * * *